(12) United States Patent
Schiaretti et al.

(10) Patent No.: US 10,583,085 B2
(45) Date of Patent: Mar. 10, 2020

(54) CARRIER PARTICLES FOR DRY POWDER FORMULATIONS FOR INHALATION

(71) Applicant: CHIESI FARMACEUTICI S.P.A., Parma (IT)

(72) Inventors: Francesca Schiaretti, Parma (IT); Francesca Buttini, Parma (IT); Ruggero Bettini, Parma (IT); Enrico Salomi, Parma (IT); Andrea Benassi, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 15/978,599

(22) Filed: May 14, 2018

(65) Prior Publication Data

US 2018/0333359 A1 Nov. 22, 2018

(30) Foreign Application Priority Data

May 17, 2017 (EP) .................................... 17171586

(51) Int. Cl.
*A61K 9/14* (2006.01)
*A61K 9/00* (2006.01)
*A61K 31/573* (2006.01)
*A61K 47/26* (2006.01)

(52) U.S. Cl.
CPC ............ *A61K 9/145* (2013.01); *A61K 9/0075* (2013.01); *A61K 31/573* (2013.01); *A61K 47/26* (2013.01)

(58) Field of Classification Search
CPC ............................. A61K 9/0078; A61K 9/0075
See application file for complete search history.

(56) References Cited

FOREIGN PATENT DOCUMENTS

WO 03/086358 10/2003
WO 2006/068484 6/2006

OTHER PUBLICATIONS

European Search Report in Application No. 17171586.5 dated Jul. 31, 2017 citing documents AO thru AAA therein, 10 pages.
Ping Du et al., "Evaluation of Granulated Lactose as a Carrier for DPI Formulations 1: Effect of Granule Size", AAPS PharmSciTech, vol. 15, No. 6 (2014) pp. 1417-1428.
Yoshiaki Kawashima et al., "Effect Of Surface Morphology Of Carrier Lactose On Dry Powder Inhalation Property Of Pranlukast Hydrate", International Journal of Pharmaceutics, vol. 172, (1998) pp. 179-188.
Jose J.B. Machado et al., "Solid-liquid equilibrium of [alpha]-lactose in ethanol/water", Fluid Phase Equilibria, vol. 173, No. 1 (200) pp. 121-134.
Anonymous: "Aulton's Pharmaceutics: The Design and Manufacture of Medicines", Elsevier Ltd., (2013) pp. 474-476.
International Search Report and Written Opinion dated Aug. 2, 2018 in PCT/EP2018/062671, citing documents AX and AY therein, 14 pages.
Ping Du et al., "Evaluation of Granulated Lactose as a Carrier for Dry Powder Inhaler Formulations 2: Effect of Drugs and Drug Loading", Journal of Pharmaceutical Sciences, XP55384672, vol. 106, No. 1, Jan. 1, 2017, pp. 366-376.
Gerald Hebbink et al., "Design of Experiments (DoE) to Determine Effect of Device and Lactose Fines on Performance of Capsule Based Dry Powder Inhalers", DFE pharma , XP002783188, Jun. 26, 2015, 1 page.

*Primary Examiner* — Jianfeng Song
(74) *Attorney, Agent, or Firm* — Oblon, McClelland, Maier & Neustadt, L.L.P.

(57) ABSTRACT

Carrier particles in the form of granules described herein are suitable for use in dry powder formulations for inhalation, and preferably administering high-strength dose active ingredients.

15 Claims, 3 Drawing Sheets

CARRIER PARTICLES FOR DRY POWDER FORMULATIONS FOR INHALATION

CROSS REFERENCES TO RELATED APPLICATIONS

This application claims priority to European Patent Application No. 17171586.5, filed on May 17, 2017, which is incorporated herein by reference in its entirety.

BACKGROUND OF THE INVENTION

Field of the Invention

The present invention relates to carrier particles in the form of granules for use in dry powder formulations for inhalation and processes for preparation thereof.

Discussion of the Background

Dry powder inhalation (DPI) drug therapy has been used for many years to treat respiratory conditions such as asthma, chronic obstructive pulmonary disease (COPD), and also systemic diseases.

Compared to oral drug intake, only relatively small doses are needed for effective therapy as first pass metabolism is by-passed and/or significantly reduced.

Such small doses reduce the body's exposure to the drug and minimize side effects. Systemic adverse effects are also reduced as topical lung delivery takes the drug directly to the site of action. Lower dosage regimens may also provide considerable cost savings, particularly where expensive therapeutic agents are concerned.

To be effectively delivered into the lungs, drug particles are required to have a particle size in the range of few micrometers, generally 1-5 microns.

Dry powder formulations are typically formulated by mixing the drug with coarse carrier particles, giving rise to ordered mixture where the micronized active particles adhere to the surface of the carrier particles whilst in the inhaler device.

The carrier makes the micronized powder less cohesive and improves its flowability, making easier handling the powder during the manufacturing process (pouring, filling dosing, etc.). Furthermore, the carrier acts as bulk agent when the therapeutic dose of the drug is in the microgram range.

During inhalation, the drug particles separate from the surface of carrier particles, and penetrate into the lower lungs, while the larger carrier particles are mostly deposited in the oropharyngeal cavity.

The detachment of drug particles from the carrier surface is regarded as the most critical factor which governs the availability of the medicament to the lungs. This will depend on the mechanical stability of the powder mix and the way this is influenced by the adhesion characteristics between the drug and the carrier and the external forces required to break up the non-covalent bonds formed between adhering particles. Too strong bonds between adhering particles may prevent indeed the separation of the micronized drug particles from the surface of carrier particles.

Different approaches aimed at modulating the adhesion have been proposed in the art to promote the release of the drug particles from the carrier particles and, hence, to increase the respirable fraction. In the art, to satisfy said purpose, the addition of fine excipient particles and/or fine additives with lubricant or anti-adherent properties (hereinafter collectively fine particles) has been suggested as a solution of the technical problem. Typically, said fine particles have a size of less than 50 microns.

On the other hand, since fine particles have poor flow properties, the flowability properties of the relevant powder formulations tend to get worse as the fine particle content increases.

In the prior art, as a solution of said technical problem, it has been proposed to use carrier coarse particles having a fissured surface capable of retaining a relatively large amount of fine particles. For example in EP 1 276 472, which is incorporated herein by reference in its entirety, carrier particles having fissures of at least 5 microns wide and at least 5 microns deep are disclosed, preferably of at least 20 microns wide and at least 20 microns deep. Although reportedly offering special advantages in the administration of active agents to be administered in relatively large doses, said technology turned to be useful for active ingredients to be administered at single doses up to 400 micrograms per shot of the inhaler.

Granulated carrier particles for DPI formulations have also been disclosed in the art, for example in WO 03/086358, Du Ping et al AAPS Pharm Sci Tech 2014, 15(6), 1417-1428, and Kawashima Y et al Int J Pharm 1998, 172, 179-188, all of which are incorporated herein by reference in their entireties.

On the other hand, the inhalatory route is more and more utilized for active ingredients such as antibiotics to be administered at higher single doses, for example equal to or higher 1 mg per shot.

This is becoming a challenging task as it is well known that higher the dose and hence concentration of the active ingredient, the higher is the risk of forming uneven agglomerates (i.e. micronized drug particles held together by strong cohesive forces) which are detrimental to the possibility of achieving a good uniformity of distribution of the drug in the powder mixture and hence a good accuracy of the dose as well as to the suitable de-aggregation upon inhalation by the patient. Moreover, the higher the dose and hence concentration of the active ingredient, the higher may be the amount of fine particles required for having a satisfying respirable fraction.

A massive presence of micronized and fine particles would have a detrimental effect on the flowability of the relevant formulation, which in turn would impact on the device capability of delivering the correct dose upon activation of the inhaler.

Therefore it would advantageous to provide carrier particles capable of accommodating higher amounts of micronized drugs and/or fine particles than the carrier particles of the prior art, without jeopardizing the flow properties of the relevant powder formulations. The problem is solved by the carrier particles of the present invention and process of preparation thereof.

SUMMARY OF THE INVENTION

Accordingly, it is one object of the present invention to provide novel carrier particles in the form of granules for use in dry powder formulations for inhalation.

It is another object of the present invention to provide novel carrier particles in the form of granules for use in dry powder formulations for inhalation which are capable of accommodating higher amounts of micronized drugs and/or fine particles than the carrier particles of the prior art, without jeopardizing the flow properties of the relevant powder formulations.

It is another object of the present invention to provide novel processes for the preparation of such particles.

These and other objects, which will become apparent during the following detailed description, have been achieved by the inventors' discovery of the granules described below.

Accordingly, in a first aspect, the present invention is directed to granules made of a physiologically acceptable excipient to be used as a carrier for dry powder formulations for inhalation, said granules having a mass diameter in the range of from 200 to 800 microns and being characterized by having on their surface pores with a perimeter from 70 to 300 microns, and a diameter from 30 to 100 microns.

In a second aspect, the present invention is directed to process for the preparation of the above granules, said process comprising the following steps:

(i) selecting particles of a physiologically acceptable excipient having a starting median volume diameter of at least 100 microns;

(ii) preparing an oversaturated aqueous solution comprising part of the physiologically acceptable excipient of step i) wherein its concentration in water is comprised between 30 and 50% w/v;

(iii) wetting the remaining particles of step i) with a 10-25% w/w of the aqueous solution of step ii);

(iv) stirring to obtain a slurry;

(v) forcing the wet mass through a proper sieve; and (vi) drying the wet mass to yield the granules.

In a third aspect, the present invention is directed to the above granules obtainable by a process comprising the steps of:

(i) selecting particles of a physiologically acceptable excipient having a starting median volume diameter of at least 100 microns;

(ii) preparing an oversaturated aqueous solution comprising part of the physiologically acceptable excipient of step i) wherein its concentration in water is comprised between 30 and 50% w/v;

(iii) wetting the remaining particles of step i) with a 10-25% w/w of the aqueous solution of step ii);

(iv) stirring to obtain a slurry;

(v) forcing the wet mass through a proper sieve; and (vi) drying the wet mass to yield the granules.

In a fourth aspect, the present invention is directed to the above granules obtained by a process comprising the steps of:

(i) selecting particles of a physiologically acceptable excipient having a starting median volume diameter of at least 100 microns;

(ii) preparing an oversaturated aqueous solution comprising part of the physiologically acceptable excipient of step i) wherein its concentration in water is comprised between 30 and 50% w/v;

(iii) wetting the remaining particles of step i) with a 10-25% w/w of the aqueous solution of step ii);

(iv) stirring to obtain a slurry;

(v) forcing the wet mass through a proper sieve; and (vi) drying the wet mass to yield the granules.

In a fifth aspect, the present invention concerns a pharmaceutical composition in form of dry powder for inhalation comprising the granules of the invention and one or more active ingredients.

In a sixth aspect, the present invention concerns a dry powder inhaler filled with the aforementioned dry powder pharmaceutical composition.

In a seventh aspect, the present invention concerns a process for preparing the aforementioned pharmaceutical composition comprising a step of mixing the carrier particles of the invention with one or more active ingredients.

In a further aspect, the present invention is also directed to a package comprising a dry powder pharmaceutical formulation according to the invention and a dry powder inhaler.

The present invention is also directed to granules made of a physiologically acceptable excipient to be used as a carrier for dry powder formulations for inhalation, said granules having a mass diameter in the range of from 200 to 800 microns and being inter alia characterized a mean rugosity coefficient of 0.6-1.0, a total intrusion volume of 0.7-1.0 $cm^3/g$, and a loading capacity equal to or higher than 35%.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
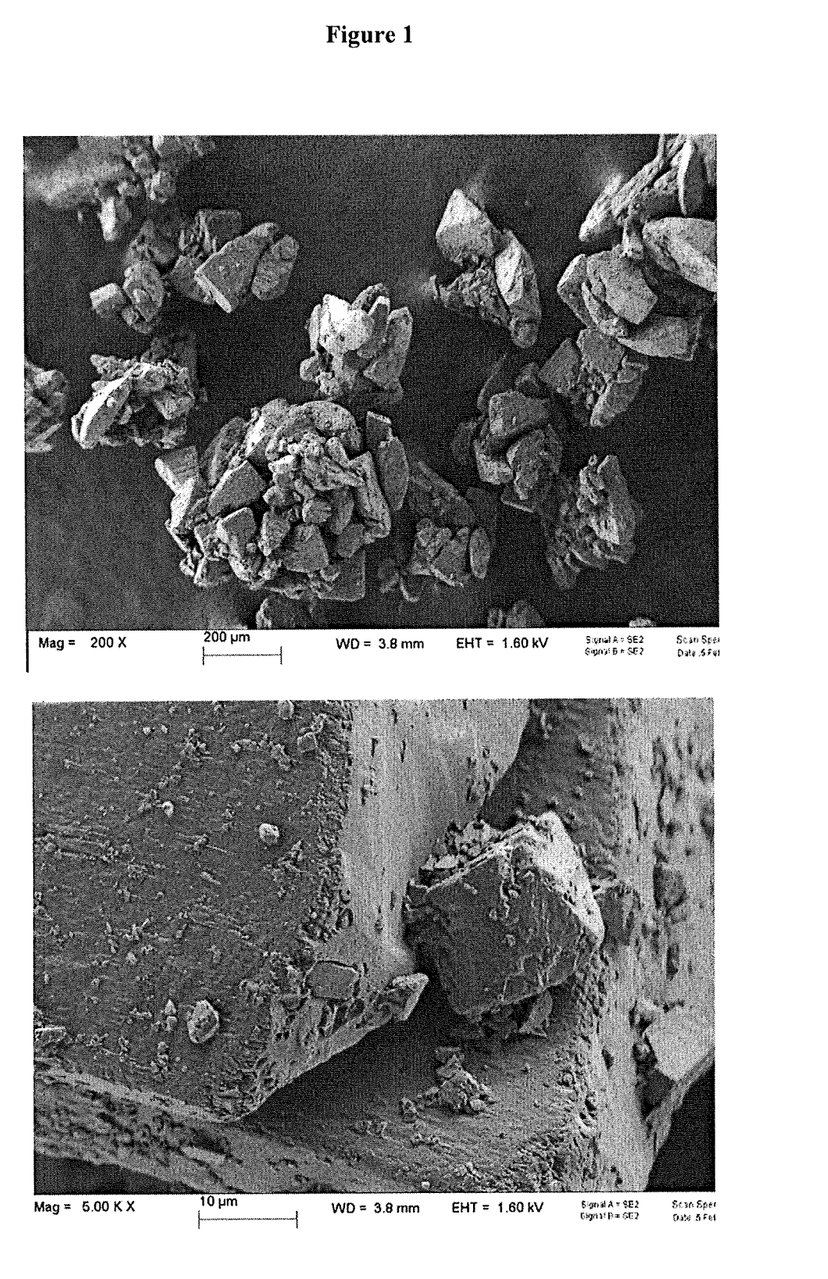
FIG. 1 shows SEM pictures of lactose granules starting from Lactohale100 at 200× (top) and 5000× (bottom) prepared with 15% almost saturated lactose aqueous solution sieved through 425 μm.
Figure 2:
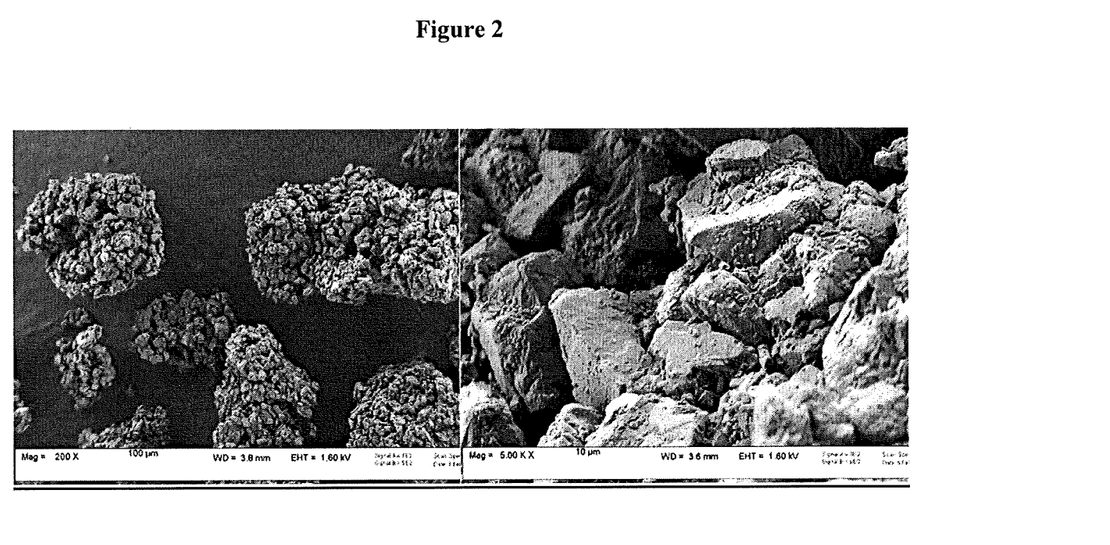
FIG. 2 shows SEM pictures of lactose granules starting from at 200× (left) and 5000× (right) prepared with 15% almost saturated lactose aqueous solution sieved through 425 μm.
Figure 3:
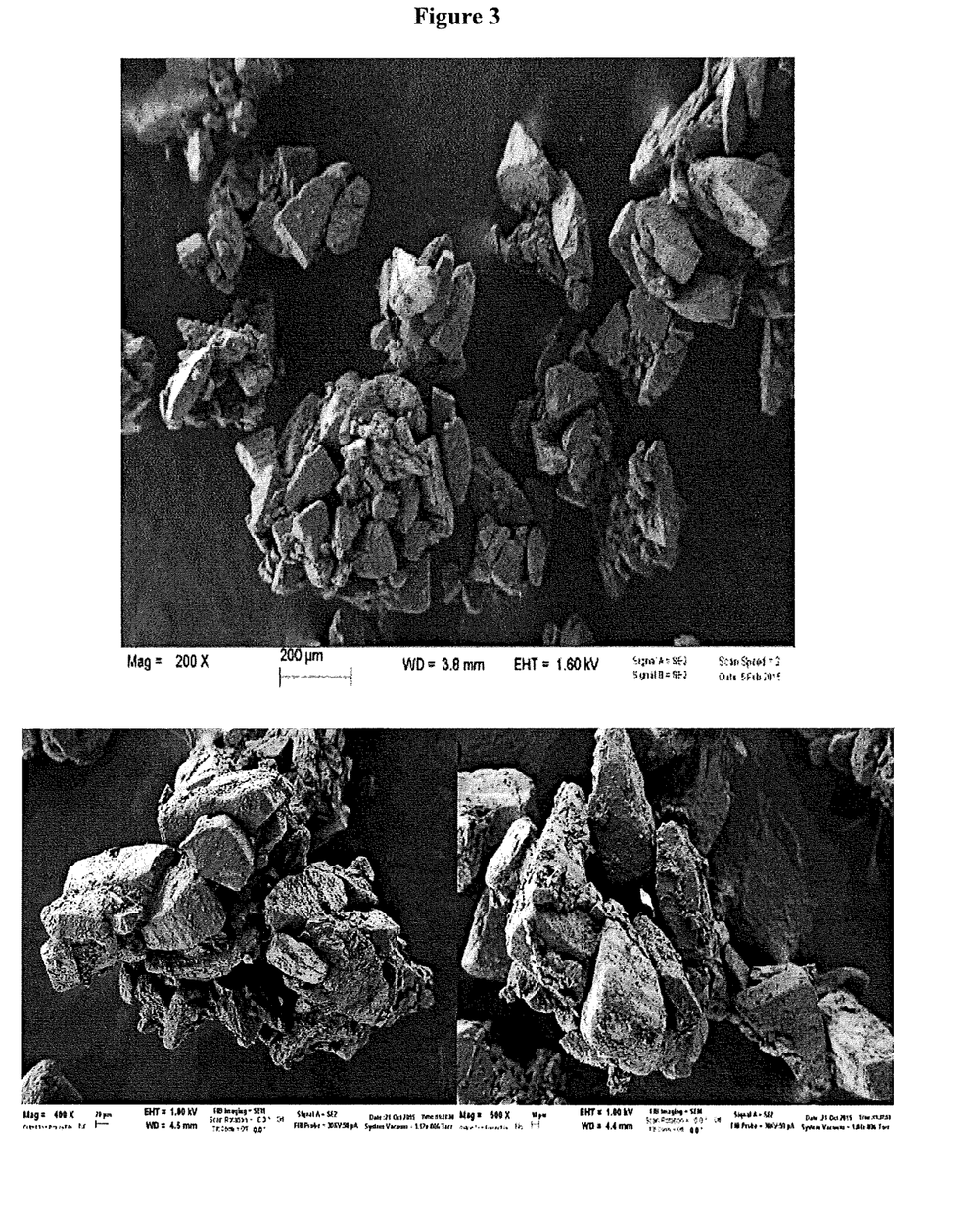
FIG. 3 shows SEM pictures of Lactohale LH100 425 μm granules; magnification for the determination of the pores 200, 400, and 500×.

Unless otherwise specified, the terms "active drug," "active ingredient," "active," "active substance," "active compound," and "therapeutic agent" are used synonymously.

The term "microns" is used as a synonym of "micrometers".

In general terms, the size of the particles is quantified by measuring a characteristic equivalent sphere diameter, known as volume diameter, by laser diffraction.

The particle size can also be quantified by measuring the mass diameter by means of suitable instruments and techniques known to the skilled person, such as sieving.

The volume diameter (VD) is related to the mass diameter (MD) by the density of the particles (assuming the size being independent from the density of the particles).

In the present application, the particle size interval of the carrier of the invention is expressed in terms of mass diameter. In particular, the particle size distribution is expressed in terms of: i) the mass median diameter (MMD) which corresponds to the diameter of 50 percent by weight of the particles, e.g. d(0.5), and ii) the mass diameter (MD) in microns of 10% and 90% of the particles, respectively, e.g d(0.1) and d(0.9).

Alternatively, the particle size may be expressed in terms of volume diameter. In particular, the particle size distribution is expressed in terms of: i) the volume median diameter (VMD) which corresponds to the diameter of 50 percent by weight of the particles, e.g d(v0.5), and ii) the volume diameter (VD) in micron of 10% and 90% of the particles, respectively, e.g d(v0.1) and d(v0.9).

With the term "fine particles" it is meant particles having a median volume diameter lower than 45 microns, preferably lower than 15 microns, made of a physiologically acceptable excipient and/or made of an additive with lubricant or anti-adherent properties, or mixture thereof.

The term "loading capacity" refers to the capability for the coarse carrier of accommodating in the pores of its surface a certain amount of fine particles.

The term "good flow properties" refers to a formulation that is easy handled during the manufacturing process and is able of ensuring an accurate and reproducible delivering of the therapeutically effective dose.

Flow characteristics can be evaluated by measuring the Can's index; a Carr's index of less than 25 is usually taken to indicate good flow characteristics.

Said flow properties can also be evaluated according to the procedure reported in Example 6.

With the term "friability" it is indicated an index of the granules strength during the mixing process with the drug particles. It is determined according to procedures known to the skilled person in the art. To be easily handled, the granules should have a friability of less than 3%, preferably of 0%.

The term "fissure index" used herein refers to the ratio of a theoretical envelope volume of the particles, as calculated from the envelope of the particles, to the actual volume of the particles that is, omitting fissures within the envelope.

The term "rugosity coefficient" is used to mean the ratio of the perimeter of a particle outline to the perimeter of the "convex hull." This measure has been used to express the lack of smoothness in the particle outline. The "convex hull" is defined as a minimum enveloping boundary fitted to a particle outline that is nowhere concave. (See "The Shape of Powder-Particle Outlines" A. E. Hawkins, Wiley, Taunton, Somerset, England: Research Studies Press, 1993, which is incorporated herein by reference in its entirety).

The expression "good homogeneity" refers to a formulation wherein, upon mixing, the content uniformity of the active ingredient, expressed as relative standard deviation (RSD), is less than 5%.

The expression "physically stable in the device before use" refers to a formulation wherein the active particles do not substantially segregate and/or detach from the surface of the carrier particles both during manufacturing of the dry powder and in the delivery device before use.

The tendency to segregate can be evaluated according to Staniforth et al. J. Pharm. Pharmacol. 34,700-706, 1982, which is incorporated herein by reference in its entirety, and it is considered acceptable if the distribution of the active ingredient in the powder formulation after the test, expressed as relative standard deviation (RSD), does not change significantly with respect to that of the formulation before the test.

The expression "respirable fraction" refers to an index of the percentage of active ingredient particles which would reach the deep lungs in a patient. The respirable fraction, also termed fine particle fraction (FPF), is commonly evaluated using a suitable in vitro apparatus, typically the Multistage Cascade Impactor or Multi Stage Liquid Impinger (MLSI), Fast Screening Impactor (FSI), according to procedures reported in common Pharmacopoeias. It is calculated by the ratio between the respirable dose and the delivered (emitted) dose.

The delivered dose is calculated from the cumulative deposition of the drug in the apparatus stages, while the respirable dose (fine particle dose) is calculated from the deposition in the stages corresponding to particles having a diameter ≤5.0 microns. The skilled person in the art shall adjust other parameters such as the inspiration flow, according to the guidelines reported in common Pharmacopeias.

A respirable fraction higher than 30% is an index of good inhalatory performance.

The term "therapeutically effective amount" means the amount of active ingredient that when delivered to the lungs via a dry powder formulation as described herein provides the desired biological effect.

By "single dose" it is meant the quantity of active ingredient administered at one time by inhalation upon actuation of the inhaler.

For actuation it is meant the release of active ingredient from the device by a single activation (e.g. mechanical or breath).

By "high single dose" it is meant a dose equal to or higher than 1 mg.

With the term "oversaturated solution", it is meant a solution wherein the physiologically acceptable excipient is dissolved at a temperature higher than room temperature giving rise to a concentration higher than the saturated concentration at room temperature.

For example, the saturated concentration of alpha-lactose monohydrate at room temperature in water is about 18-19% w/v, while the saturated concentration of mannitol at room temperature in water is about 18-21% w/v. When both solutions are heated at 50° C., a concentration of about 40-43% w/v is achieved.

The invention is directed to granules made of a physiologically acceptable excipient to be used as a carrier for dry powder formulations for inhalation being characterized by having on their surface pores with a perimeter of from 70 to 300 microns, preferably from 100 to 200 microns, and a diameter of from 30 to 100 microns.

Advantageously, the pores may be 40 to 80 microns deep. Preferably, the perimeter of the pores is about 100 to 220 micron and their diameter is from 40 to 80 micron.

The perimeter, the diameter and the deep of the pores could be determined according to procedure reported in Example 2.

The physiologically acceptable excipient may be selected from the group consisting of lactose, mannitol, trehalose, dextran, and glucose.

Advantageously, the granules may consist of alpha-lactose or the solvate thereof or beta-lactose.

In another embodiment, the granules may consist of mannitol.

Preferably, the granules consist of alpha-lactose monohydrate.

All of the granules have a particle size, expressed as mass diameter, in the range of from 200 to 800 microns, preferably of 300 to 600 microns, more preferably 400 to 500 microns.

When expressed as volume diameter, the particle size distribution of the granules shall fulfil the following parameters: d(v,0.1) 210 to 250 microns, d(v,0.5) 400 to 600 microns and d(v,0.9) 700 to 750 microns.

A number of other methods may also be used to determine the characteristics of the granules of the invention, for example tapped density, porosimetry, the fissure index, the rugosity coefficient and the Specific Surface Area.

The tapped density of the granules of the invention could be measured according to European Pharmacopeia Ed. 7.0, 2.9.34, which is incorporated herein by reference in its entirety. Typically, when made of alpha-lactose monohydrate, it is not more than 0.6 g/ml, preferably not more than 0.55 g/ml, more preferably 0.4 to 0.55 g/ml.

Otherwise it might be measured as follows: a measuring cylinder is weighed on a top pan balance (2 place). Approximately 50 g powder is introduced into the measuring cylinder, and the weight is recorded. The measuring cylinder containing the powder is attached to a jolting volumeter (Jel Stampfvolumeter). The jolting volumeter is set to tap 200 times. During each tap, the measuring cylinder is raised and allowed to fall a set distance. After the 200 taps, the volume of the powder is measured. The tapping is repeated and the new volume measured. The tapping is continued until the powder will settle no more. The tapped density is calculated as the weight of the powder divided by the final tap volume. The procedure is performed three times (with new powder each time) for each powder measured, and the mean tapped density calculated from those three final tapped volume values.

Porosimetry is typically measured by Mercury intrusion porosimetry.

Typically, parameters used for measurements are as follows: sample cell is 1.0×3.0 cm, pressure range is 0.5 to 33000 psi, pore size range is 0.0064 to 950 μm, contact angle of mercury is 140 degrees, and surface tension of mercury is 0.48 N/m (480 dyn/cm), for example, using an PoreMaster 33 system (Quantchrome Instruments, FL, USA). Samples should be evacuated to below 5 Pa prior to analysis to remove air and loosely bound surface water.

Advantageously, the granules of the invention are characterized by a total intrusion volume measured by Mercury intrusion porosimetry of 0.7 to 1.0 cm$^3$/g, preferably of 0.8 to 0.95 cm$^3$/g.

The fissure index is typically calculated from the ratio of a theoretical envelope volume of the particles, as calculated from the envelope of the particles, to the actual volume of the particles that is omitting fissures within the envelope. The theoretical envelope volume may be determined optically, for example, by examining a small sample of the particles using an electron microscope. The theoretical envelope volume of the particles may be estimated via the following method. An electron micrograph of the sample may be divided into a number of grid squares of approximately equal populations, each containing a representative sample of the particles. The population of one or more grids may then be examined and the envelope encompassing each of the particles determined visually as follows. The Feret diameter for particles within a grid is measured relative to a fixed axis of the image. Typically at least ten particles are measured for their Feret diameter. Feret diameter is defined as the length of the projection of a particle along a given reference line as the distance between the extreme left and right tangents that are perpendicular to the reference line. A mean Feret diameter is derived. A theoretical mean envelope volume may then be calculated from this mean diameter to give a representative value for all the grid squares and thus the whole sample. Division of that value by the number of particles gives the mean value per particle. The actual volume of the particles may then be calculated as follows. First, the mean mass of a particle is calculated. A sample of approximately 50 mg is taken and its precise weight recorded to 0.1 mg. Then by optical microscopy the precise number of particles in that sample is determined. The mean mass of one particle can then be determined. The procedure is then repeated five times to obtain a mean value of this mean. Second, a fixed mass of particles (typically 50 g) is weighed out accurately, and the number of particles within this mass is calculated using the above mean mass value of one particle. Finally, the sample of particles is immersed in a liquid in which the particles are insoluble and, after agitation to remove trapped air, the amount of liquid displaced is measured. From this the mean actual volume of one particle can be calculated.

The mean rugosity coefficient may be calculated optically as follows. A sample of particles should be identified from an electron micrograph or from an optical micrograph as identified above. For each particle the perimeter of the particle outline and the associated perimeter of the "convex hull" is measured to provide the rugosity coefficient. This should be repeated for at least ten particles to obtain a mean value.

Advantageously, the mean rugosity coefficient of the granules of the invention is from 0.6 to 1.0, preferably 0.7 to 0.9.

From the above determination, the elongation coefficient could also be determined according to Mikli et al. (V. Mikli, H. Kaerdi, P. Kulu, M. Besterci Proc. Estonian Acad. Sci. Eng. 7 (2001) 22-24) or Hryciw et al. (R. D. Hryciw, M. Asce, J. Zheng, S. M. Asce, K. Shetler, S. M. Asce Journal of Geotechnical and Geoenvironmental Engineering 142 (2016) 04016038, which are incorporated herein by reference in their entireties).

Advantageously, the elongation index of the granules of the invention is from 0.3 and 1.0, preferably 0.35 to 0.9.

The Specific Surface Area could be determined by Brunauer-Emmett-Teller (BET) nitrogen adsorption method according to a known procedure.

The Specific Surface Area of the granules of the invention, when consisting of alpha-lactose monohydrate, is from 0.13 and 0.20 m$^2$/g, preferably from 0.14 to 0.16 m$^2$/g.

Each granule has a characteristic desert rose or rosette shape and is in the form of an agglomerate consisting of a plurality of crystals fused to one another in which crystals within an agglomerate become fused to one another by solid bridges.

The above granules have substantially no tendency to disintegrate during handling and/or the powder is stored into the inhaler device. Their friability is indeed less than 3%, preferably less than 2%, more preferably of 0%, as determined.

The friability of the granules could be determined using a modified friability test for tablets (Ph. Eur. 8.0 2.9.7, which is incorporated herein by reference in its entirety). The friability test can be carried out by substituting the standard drum of the friabilometer described in the Pharmacopoeia with a cylindrical jar having a volume of 100 ml rotating around its main axes. About 20 grams of granules are accurately weighed and loaded in the jar; then the apparatus is operated at 100 rpm for 4 minutes. Thereafter, a sieve of 180 micron nominal opening is weighed (initial weight) and the granules are sieved through it; the weight of the sieve after this procedure is recorded (final weight). The amount of powder remaining on the sieve expressed in grams is determined as the difference between the final and the initial weight.

The friability % is calculated as:

$$\frac{20 - \text{amount of powder remaining on the sieve}}{20} \times 100$$

However, contrary to what reported for the carrier particles disclosed in EP 1276472, which is incorporated herein by reference in its entirety, at certain air flow pressures, the granules of the invention tend to disintegrate upon expulsion from the inhaler. Without being limited by the theory, this is considered an advantage as the particles of the active ingredient could be released more rapidly from the carrier and hence available to exert their therapeutic effect more efficiently.

Said optimal strength characteristics are the results of the process utilized for preparing the granules.

Therefore, according to another aspect, the present invention is directed to a process comprising the following steps:

(i) selecting particles of a physiologically acceptable excipient having a suitable starting median volume diameter;

(ii) preparing an oversaturated aqueous solution comprising part of the physiologically acceptable excipient of step i) wherein its concentration in water is comprised between 30 and 50% w/v;

(iii) wetting the remaining particles of step i) with a 10-25% w/w of the aqueous solution of step ii);

(iv) stirring to obtain a slurry;

(v) forcing the wet mass through a proper sieve; and (vi) drying the wet mass to yield the granules.

Advantageously, the particles of the starting material in step i) have a median volume diameter of at least 100 microns, preferably from 120 micron to 300 microns, more preferably from 150 to 250 microns.

In a preferred embodiment of the invention, all the particles have a volume diameter of 30 and 400 microns, more preferably with the d(v,10) of 45 to 65 microns and d(v,90) of 300 to 350 microns.

In a particular embodiment of the present invention, said starting powder may optionally comprise a suitable amount of fine particles of the same physiologically acceptable excipient.

In an alternative embodiment, a suitable amount of fine particles of the same physiologically acceptable excipient could be added to the obtained granules if step vi).

In step ii), an oversaturated aqueous solution of the same physiologically acceptable excipient used as carrier is prepared, preferably alpha-lactose monohydrate or mannitol, more preferably alpha-lactose monohydrate.

For example, by heating at 50° C., a concentration in water of alpha-lactose monohydrate of 35% w/v could be achieved.

The aqueous solution of step ii) shall be added in an amount of 10 to 25% w/w with respect to the amount of the above particles, preferably ranging from 13 to 22% w/w. It has been indeed found that, if granulation is carried out using an oversaturated solution of the physiologically acceptable excipient as herewith defined, the obtained granules show improved properties in terms of friability, allowing an easier handing when blended in conventional mixers.

In step iv) the starting particles and the aqueous solution of step iii) are stirred until a slurry, wet mass, is obtained with a homogeneous aspect.

Typically, stirring is carried out in a suitable apparatus, such a mortar, for 10 to 15 minutes.

However, the skilled person may choose different apparatus and processing conditions according to its knowledge.

Advantageously, the wet mass, obtained in step iv), in step v) is forced through a sieve having mesh of 212 to 600 microns, preferably of 425 microns.

In step vi), the wet granules are then dried according to procedures known to the skilled person in the art. Advantageously the granules are dried either in a microwave or in an oven under vacuum. If a microwave is utilized, typically the wet granules are dried at 200 to 650 W, preferably at 600 W for 2 to 10 minutes, advantageously for 3 to 8 minutes, preferably for 4 to 6 minutes.

If alternatively, an over under vacuum is used, typically the wet granules are dried at 40 to 80° C., preferably at 50 to 70° C., more preferably at 60° C., at a pressure of 300 to 100 mbar, preferably at 200 mbar for 15 to 60 minutes, preferably for 25 to 45 minutes.

The granules of the invention exhibit good flow properties as they have a Carr index well lower than the value of 25, which is usually taken as discriminating value for free flowing powders.

In a particular embodiment of the present invention, a suitable amount of fine particles of the same or a different physiologically acceptable excipient may be added.

In fact, it was found that the granules of the invention, due to their surface characteristics, are capable of retaining a relatively large amount of fine particles, substantially without segregation, and so maintaining good flow properties even in the presence of an amount of fine particles equal to or higher than 35% and an amount of micronized active ingredient equal to or higher than 10%.

The granules of the present invention have indeed shown a loading capacity much higher than the carriers of the prior art, and advantageously equal to or higher than 35% of fines particles weight to carrier weight. The loading capacity for a given carrier can be estimated according to the method reported in the Example 10. The skilled person in the art shall replace the used materials with other suitable ones.

It follows that the corresponding pharmaceutical formulations in form of dry powders are physically stable.

The pharmaceutical formulations comprising the granules of the present invention, optionally in the presence of fine particles, also exhibit a good homogeneity of active ingredients to be delivered at high doses, for example at 1 mg per shot of the inhaler as well as good aerosol performances.

Therefore, the invention is directed to a pharmaceutical composition in form of dry powder for inhalation comprising the carrier granules of the invention and one or more active ingredients.

The active ingredient may be practically any pharmaceutically active compound which can be administered by inhalation in dry powders.

In order that the active substance is inhalable, i.e. it can pass into the deep lung such as the terminal and respiratory bronchioles and the alveolar ducts and sacs, it must be in particulate form having a mean particle diameter (measured as the mass mean diameter) of at most about 10 microns, e. g. from 1 to 10 microns, and preferably 1 to 6 microns. Such micronized particles may be obtained in a manner known per se, for example by micronization, controlled precipitation from selected solvents, spray drying, supercritical fluids, or according to the processes described in WO 2004/073827, WO 2008/155570, WO 2008/114052, and WO 2010/007447, all of which are incorporated herein by reference in their entireties.

The therapeutically amount of the active substance may vary within wide limits depending on the nature of the active substance, the type and severity of the condition to be treated and the condition of the patient in need of treatment.

Typically, the active substance particles are added to the carrier particles of the invention by mixing. The particles may be mixed using a tumbling blender, for example a Turbula™ mixer, according to known procedures.

In particular, the rotation speed of the mixer and the time of mixing shall be adjusted by the skilled person to obtain a good uniformity of distribution of the active ingredient in the formulation.

An excellent uniformity of distribution of the active ingredient is achieved when said active ingredient has a particle size distribution wherein no more than 10% of the particles have a volume diameter [d(v,0.1)] lower than 0.6 microns, preferably lower than 0.8 microns, and no more than 50% of particles have a volume diameter [d(v,0.5)] of 1.6 to 2.5 microns.

As an example, they may be chosen from short-acting and long-acting beta$_2$-agonists such as terbutalin, reproterol, salbutamol, salmeterol, formoterol, carmoterol, milveterol, indacaterol, olodaterol, fenoterol, clenbuterol, bambuterol, broxaterol, epinephrin, isoprenaline or hexoprenaline or salts and/or solvate forms thereof; short-acting and long-acting anticholinergics such as tiotropium, ipratropium, oxitropium, oxybutynin, aclidinium, trospium, glycopyrronium, or the compounds known with the codes GSK 573719 and GSK 1160274, in form of salts and/or solvate forms thereof; bifunctional Muscarinic Antagonist-beta2 Agonist (MABA) compounds for inhalation such as GSK 961081; short-acting and long acting corticosteroids such as butixocart, rofleponide, flunisolide budesonide, ciclesonide, mometasone and its ester, i.e. furoate, fluticasone and its ester, i.e. propionate and furoate, beclomethasone and its ester, i.e. propionate, loteprednol or triamcinolone acetonide and solvate forms thereof; leukotriene-antagonists, such as andolast, iralukast, pranlukast, imitrodast, seratrodast, zileuton, zafirlukast or montelukast; phosphodiesterase-inhibitors, such as filaminast, piclamilast or roflumilast; an PAF-Inhibitor, such as apafant, rorapafant or israpafant; pain killers such as morphine, fentanyl, pentazocine, buprenorphine, pethidine, tilidine, or methadone; potency agents such as sildenafil, alprostadil or phentolamine; or a pharmaceutically acceptable derivative or salt of any of the foregoing compounds or classes of compounds. In as much as any of these compounds possess chiral centers, the compounds can be used in optically pure form, or can be presented as diastereomeric mixtures or racemic mixtures.

Dry powder formulations may also employ proteins, peptides, oligopeptides, polypeptides, polyamino acids nucleic acid, polynucleotides, oligo-nucleotides and high molecular weight polysaccharides.

In a particular embodiment of the present invention, the dry powder formulations comprising the granules of the invention are useful for the administration of active ingredients to be delivered at single doses per actuation of the inhaler of 1 mg or higher, i.e. 2 mg, 5 mg or more.

Examples are antibiotics such as ciprofloxacin, levofloxacin and colistin, tobramycin, amikacin and gentamicin; proteins such as insulin and al-antitrypsin; antiviral drugs such as zanamivir and ribavirin; antifungal agents such as itraconazole, and phosphodiesterase (PDE)-5 inhibitors such as sildenafil and tadalafil.

The concentration of the active ingredient in the powder formulation will depend on the shot weight of the formulation delivered upon actuation of the inhaler.

For example, considering an expected single dose of 1 mg, if the shot weight of the formulation delivered upon actuation of the inhaler is 10 mg, this would correspond to a concentration of the active ingredient of 10% w/w. Analogously, for a shot weight of 5 mg, the concentration of the active ingredient would be of 20% w/v, while for a shot weight of 20 mg, the concentration of the active ingredient would be of 5%.

In a preferred embodiment, the dry powder formulations comprising the granules of the invention are particularly useful for the administration of active ingredients to be delivered at single doses per actuation of the inhaler of from 1 mg to 40 mg.

In a particular embodiment of the present invention, the powder formulation further comprises a fraction of fine particles having a median volume diameter lower than 45 microns, more advantageously lower than 15 microns, preferably lower than 10 microns, in an amount higher than 10%, preferably higher than 30%, more preferably higher than 50% based on the weight of the formulation.

Said fine particles may be made of a physiologically acceptable excipient as defined above and/or may be made of an additive material selected from the class of the anti-adherents such as the amino acids, for example leucine and isoleucine, or from the class of lubricants such as magnesium stearate; sodium stearyl fumarate, stearyl alcohol, stearic acid, and sucrose monopalmitate.

In particular embodiment, the fine particles are composed of particles of a physiologically acceptable excipient and particles of an additive in any ratio, and they are prepared according to the teaching of WO 01/78695, which is incorporated herein by reference in its entirety.

In an even more preferred embodiment, the fine particles consist of a mixture of 90 to 99.5 percent by weight of particles of alpha-lactose monohydrate and 0.5 to 10 percent by weight of magnesium stearate, wherein at least 90% of said particles have a volume diameter lower than 12 microns, and the volume median diameter of said particles is from 4 and 6 microns.

Said fine particles could be added to the formulation and mixed according to known methods.

The dry powder formulation for inhalation comprising the carrier granules of the invention may be utilized with any dry powder inhaler.

Dry powder inhalers can mainly be divided in: i) single-dose (unit-dose) inhalers, for the administration of single subdivided doses of the active compound; and ii) pre-metered multi-dose inhalers or reservoir inhalers pre-loaded with quantities of active principles sufficient for longer treatment cycles.

The dry powder formulations may be presented in unit dosage form. Dry powder compositions for topical delivery to the lung by inhalation may, for example, be presented in capsules and cartridges of for example gelatin, or blisters of for example laminated aluminum foil, for use in an inhaler or an insufflator.

The dry powder formulation for inhalation according to the present invention is particularly suitable for multi-dose dry powder inhalers comprising a reservoir from which individual therapeutic dosages can be withdrawn on demand through actuation of the device.

A preferred multi-dose device is the inhaler described in WO 2004/012801, which is incorporated herein by reference in its entirety, in particular from page 1, first line, to page 39, last line.

Other multi-dose devices that may be used are for instance the ELLIPTA™ or DISKUS™ of GlaxoSmithKline, the TURBOHALER™ of AstraZeneca, TWISTHALER™ of Schering and CLICKHALER™ of Innovata.

As marketed examples of single-dose devices, there may be mentioned ROTOHALER™ of GlaxoSmithKline and HANDIHALER™ of Boehringer Ingelheim.

In another embodiment, the present invention provides a method for treating a disease of the respiratory tract by administering an effective amount of the formulation of the present invention. Specific examples of the disease of the respiratory tract which may be treated include asthma and COPD.

For example, in the case of asthma, the active ingredient may be any one or more of long-acting beta2-agonists and/or corticosteroids, and the active ingredient is contained in the pharmaceutical composition in an amount sufficient to deliver a dose of 1 mg to 2 mg per actuation of the dry powder inhaler.

Analogously, in the case of chronic obstructive pulmonary disease (COPD), the active ingredient may be any one or more of long-acting beta2-agonists and/or corticosteroids, and/or long-acting anticholinergics, and/or MABA, and the active ingredient is contained in the pharmaceutical composition in an amount sufficient to deliver a dose of 1 mg to 2 m per actuation of the dry powder inhaler.

Other features of the invention will become apparent in the course of the following descriptions of exemplary embodiments which are given for illustration of the invention and are not intended to be limiting thereof.

EXAMPLES

Example 1—Materials

Three alpha-lactose monohydrate lactose powders were used as starting materials: Lactohale-LH100 and Respitose ML006 were provided by DFE Pharma GmbH (Germany) while Capsulac 60 was provided by Meggle Group Wasserburg GmbH (Germany), then sieved to obtain a fraction with a mass diameter of 212-355 micron. Table 1 reports the particle size distribution of these materials according to the producer.

TABLE 1

| | dv10 (μm) | dv50 (μm) | dv90 (μm) |
|---|---|---|---|
| Lactohale LH100 | 45 to 65 | 125 to 145 | 200 to 245 |
| Respitose ML006 | 2 | 17 | 45 |
| sieved Capsulac 60 | 130 to 180 | 230 to 290 | 320 to 370 |

Beclometasone dipropionate (BDP) was provided by Farmabios SpA (Italy).

Magnesium stearate (MgSt) was provided by Peter Greven GmbH (Germany).

As fine particles, alpha-lactose monohydrate Lactohale LH300 (dv50<5 μm) was purchased by DFE Pharma (Germany).

A mixture constituted by 98% w/w of fine alpha-lactose monohydrate particles and 2% w/w of MgSt was prepared according to the process disclosed in WO 01/78693, which is incorporated herein by reference in its entirety (hereinafter the Preblend).

Example 2—Microwave Preparation of Lactose Granules Using an Almost Saturated Lactose Solution as Binder As the friability of the samples produced with water solution as a binder was in all cases too high, water was substituted with a lactose solution as a binder. Lactose preparation was carried out by mixing the lactose powder with 15% (w/w) of an almost saturated lactose solution as a binder instead of water. The almost saturated lactose solution was prepared by dissolving under stirring at 50° C., 3.5 g of lactose in 10 mL of ultrapure water (resistivity=1-10 MΩ cm, conductivity=1-0.1 μS/cm). Thereafter the slurry was prepared and was granulated by forcing the wet mass through either a 212 μm or a 425 μm sieve. The obtained granules were then dried in the microwave at 600 W for 5 minutes.

This procedure was carried out with two types of lactose as staring material for the granules production: Respitose ML006 having particle size lower than 125 μm (dv50 17.0 μm) and Lactohale LH100 (dv50 125-145 μm).

The friability test carried out on samples forced to a 425 μm and that 212 μm sieve had a friability of 0% and 33% respectively. The friability outcomes indicate that the almost saturated lactose solution used as a binder increased the granules strength. This behavior is due to the fact that the lactose in the solution creates bridges between the lactose particles during dried, thus increasing the granules hardness.

The lactose carrier morphology was also investigated by scanning electron microscopy (SEM). It was assessed by using a SEM SUPRA 40 (Carl Zeiss, Germany). Each powder sample (10 mg) was placed on a conductive sample holder previously covered with a double-sided conductive carbon tape so as to allow the dispersion of the charge. Particles in excess were removed by a gentle flow of nitrogen. The samples were analyzed in high vacuum conditions $10^{-6}$ mbar and the images were collected at the same magnitude 200× of magnification using an acceleration voltage of 1.0 kV. FIGS. 1 and 2 show the SEM pictures of the granules forced through 425 μM, starting from Lactohale LH100 and Respitose ML006, respectively.

It can be noted that the lactose aggregates of Lactohale LH100 exhibited large inter-particles spaces due the greater particle size of the starting material (dv50=125 μm) compared to Respitose granules that show a more compact structure with narrower and lesser deep inter-particles spaces.

Morphological analysis was also performed in order to evaluate the porosity of the material, i.e. the size of the holes that were created among the lactose particles in the production process. The integrity of the granules was checked as well. It has been reported that one of the factors that dominates the drug-carrier adhesion is the presence of "holes" and cavity on the lactose surface. In particular, "active sites" may be considered as areas on the lactose surface that have a high adhesion potential; drug particles adhered to these areas will subsequently be more difficult removed during the aerosolization step. Furthermore, the adhesion force increases in the presence of an irregular carrier surface (presence of pits and cliffs) or due to larger surface area which increases the points of contact with the drug particles.

The perimeter and the Feret diameter of the holes were calculated from the SEM pictures using the open source image processing and analysis software IMAGE-J® (National Institute of Health, USA, download at https://imagej.nih.gov/ij/).

The scale of the measurements was set by transforming the number of pixels constituting a line of know length in μm using the menu command analyse, set scale; moreover global command in set scale was checked so as the scale defined was used for all pictures analyzed in the same work session. In order to obtain reliable result, 110 pictures were analyzed and three holes for each picture were evaluated using the tool freehand selection that allows to select the perimeter of the holes. Then, the perimeter and the Feret diameter (defined by Image-J user guide as "The longest distance between any two points along the selection boundary, also known as maximum caliper") were acquired by the menu command analyse, measurement. Perimeter and Feret diameter were previously set using the menu command analyse, set measurement.

The mean values of perimeter and Feret diameter of the pores were 146.6±66.4 μm and 52.0±23.8 μm respectively.

A more comprehensive statistical analysis of the particle morphology has been performed using optical microscopy (Nikon AZ 100M) in combination with image analysis tools (NIS-Elements AR suite from Nikon) over a large population of thousands of carrier particles. The deviation of the particle shape from an ideal circle is described by the "elongation coefficient", this is calculated as the ration of the minim to the maximum Feret diameter. To estimate the minimum and maximum Feret diameter the software rotates the projection axis from 0 to 180 degrees with 10 degrees step. The "elongation coefficient" distribution is centered on about 0.55 ranges from 0.35 to 0.9. The particle size has been characterized by an equivalent diameter, i.e. the diameter of a circle having the same area of each carrier particle. This value is centered on about 650 μm and spans the interval 270 to 900 μm.

Example 3—Vacuum Oven Preparation of Lactose Granules Using an Almost Saturated Lactose Solution as Binder The alpha-lactose monohydrate raw material was wetted with a 15% w/w almost saturated lactose solution. The slurry was granulated passing through a 425 μm sieve and then the granules were dried in an oven (Gallenkamp, Fistreem International LTD, UK) for 30 minutes at 60° C. with vacuum of 200 mbar residual pressure. The samples were then weighted in order to evaluate the weight loss, hence, the drying was repeated for 5 minutes in order to assess that no further weight loss occurred.

Example 4—Microwave Preparation of Lactose Granules According to the Present Invention+Fine Lactose Particles The addition of a portion of fine lactose particles to the carrier granules of the invention was investigated in order to improve the respirability of the drug. The portion of fine lactose <45 μm was added at 10% w/w, 30% w/w and 50/% w/w directly to the dried LH100 granules (425 μm size) after the slurry preparation was carried out as described in Example 2. Alternatively, a portion of 10% w/w of the Preblend, as defined above, was added.

Example 5—High Drug Doses Blends

Both binary and ternary BDP blends (size batch 5 g) containing 10% drug were prepared according to a 4 steps procedure:
sieving 0.5 g of BDP with half part of the carrier; BDP/carrier was gently forced through a 600 μm sieve.
Thereafter the remain part of the carrier was added;
mixing in Turbula® mixer for 30 min at 32 rpm;
sieving again through 600 μm; and
mixing with Turbula® for other 15 min.
In the case of ternary mixture, the carrier was constituted by a blend of course and fine lactose prepared by pre-mixing them in Turbula® for 2 hours at 32 rpm. The homogeneity of the prepared mixtures was checked at the end of the mixing procedure. For each formulation five samples (20 mg each) were collected from different spots of the powder bed. Each sample was dissolved in 50 mL of an appropriate solvent (water in the case of salbutamol sulphate, an ethanol/water 60:40 v/v solution in the case of BDP) and the quantification of the drug was performed. Homogeneity was assumed at a coefficient of variation (calculated as the percentage of the ratio between standard deviation and mean value on the five measurements) lower than 5%.

As far as all the binary and ternary blends, the drug content was quite homogeneous, and the relative standard deviation was lower than 5%.

Example 6—Powder Flowability and Specific Surface Area of the Granules of the Present Invention Powder flowability was performed using a FT4 powder rheometer (Freeman Technology, UK). In this study, powder flowability was investigated using the powder rheometer in the dynamic mode. In dynamic mode, a blade with a diameter of 23.5 mm was traversed through the 25 ml samples in a 25 mm diameter borosilicate glass vessel with a blade tip speed of 100 mm/s and a helix angle of −5°. The energy (mJ) required to move the blade through the powder during a downward traverse, namely from the top to the bottom of the vessel, was defined as basic flowability energy (BFE). Furthermore, the specific energy (SE), that is the energy (mJ) per gram established on the upward traverse, was measured; in this case the powder was unconfined (powder can lift up) and so the energies measured were more depending on the cohesive and mechanical interlocking forces between the particles and less influenced by other factors such as the compressibility that can be very significant in the BFE test.

All samples before the measurement were pre-conditioned using the instrument's "conditioning" process. The "conditioning" blade action gently disturbs the powder bed and creates a uniform and slightly packed test sample in order to remove any pre-compaction and excess of air from the sample.

The rheological properties of the prepared granules were investigated with the FT4 apparatus. The flowability of Lactohale LH100 raw material was determined for comparative purpose.

Table 2 reports the Basic Flowability Energy (mJ) and the Specific Energy (mJ) of the powder samples. Interestingly a marked difference between the raw material and treated material can be observed. The BFE of the treated samples were significantly lower than that of the raw material indicating better flow property compared to the raw material. The reason of this behaviour can be easily attributed to the particle higher size of the carrier, considering that particles with a low particle size are more cohesive and thus require more energy to flow. Good results were obtained with both the LH100 granules 425 μm and the LH 100 granules 425 μm+30% of "fine" particles added to the starting material before the granulation step. Even lower values of BFE were obtained with the latter granules.

These data are in agreement and confirm the data relevant to the granule strength determined with the dispersibility test: in this case, the carrier remained intact after the stress imposed by the blade of the powder rheometer indicating that it was not subjected to the segregation phenomenon that has a detrimental effect on the BFE.

The specific energy is mostly related to the particle cohesion, so in general a SE lower than 5 indicates low particle cohesion, a SE between 5 and 10 indicates a moderate cohesion and SE higher than 10 indicates a higher particle cohesion. The obtained SE values are reported in Table 2. It can be appreciated that all granules showed a SE lower than 5 while the value relevant to the raw material was slightly higher than 5. This data indicate a lower particle cohesion of the treated materials also in this case ascribable to the particle size of this carriers and further confirm the BFE results previously described.

TABLE 2

|  | BFE (mJ) | SE (mJ/g) |
|---|---|---|
| LH100 raw material | 455 ± 31.8 | 5.3 ± 0.1 |
| LH100 Granules | 188 ± 33.8 | 3.2 ± 0.9 |
| LH100 + 30% 45 μm | 148 ± 28.0 | 3.1 ± 0.1 |

The specific surface area (SSA) was evaluated in order to understand if the addition of "fine" could fill the spaces present in the lactose granules. The specific surface area of the carriers was investigated using the Micromeritics Tristar II 3020 (Norcross, USA). All samples were vacuum dried for two days at 25° C. using the Micromeritics VacPrep 061 degas unit (Norcross, USA). The measurements were performed using nitrogen adsorption and desorption isotherms at the temperature of liquid $N_2$ (−196° C.); Brunauer, Emmett, and Teller (BET) (Emmett, 1936) adsorption theory was used to calculate the specific surface area, using a pressure range of 0.05 to 0.30 normalized to the saturation pressure of the adsorbate.

1.5 g of powder was used, resulting in BET correlation factors above 0.999, indicating applicability of the method. Each measurement was carried out in triplicate. The specific surface area (SSA) analysis was conducted on LH100 425 μm granules, LH100 425 μm granules+10% of 45 μm "fine" particles, and LH100 425 μm granules+30% of 45 μm "fine" particles. The results are reported in Table 3. As it was expected, the increase of the percentage of "fine" increased the specific surface area of the carrier.

TABLE 3

|  | LH100 ($m^2/g$) | LH100 + 10% <45 μm ($m^2/g$) | LH100 + 30% <45 μm ($m^2/g$) | fine <45 μm ($m^2/g$) |
|---|---|---|---|---|
|  | 0.1542 | 0.213 | 0.2915 | 0.6222 |
|  | 0.1417 | 0.2285 | 0.3446 | 0.6475 |
|  | 0.1643 | 0.2182 | 0.3102 | 0.6796 |
| Mean | 0.1534 | 0.2199 | 0.3154 | 0.6498 |
| S.D. | 0.0113 | 0.0079 | 0.0269 | 0.0288 |

Example 7—In Vitro Aerodynamic Assessment

In vitro aerodynamic assessment was performed using a Fast Screening Impactor (FSI, Copley Scientific, UK). This equipment employs two segregation stages: a Coarse Particle Mass (CFC) collecting particles with an aerodynamic diameter larger than 5 μm and Fine Particle Mass (FPM) collecting particles with an aerodynamic diameter lower than 5 μm. The FSI is composed by an Induction Port (IP), a Coarse Fraction Collector (CFC) filled with 10 mL methanol-water 60:40 v/v, that acted as a liquid trap for the non-inhalable particles and by a Fine Fraction collector (FFC) fitted with a glass fibre filter (Type A/E, Pall Corporation, USA).

After completing the assembly, the FSI was connected to a VP 1000 vacuum pump (Erweka, Germany) and the flow rate through the impactor was measured by a mass flowmeter (model 3063, TSI, USA). A medium resistance single-dose DPI, RS01® (Plastiape S.P.A., Italy), was chosen as aerosolization device. For each mixture, three Quali-V-I® capsules size 3 (Qualicaps®, Spain) were filled with 10.0±0.1 mg of powder, introduced in the inhaler device, and finally pierced. Once connected the device to the impactor through an airtight rubber mouth, the vacuum pump was activated at a flow of 60 L/min for 4 seconds so that 4 L of air were drawn through the apparatus according to Ph. Eur. 8.0, 2.9.18, which is incorporated herein by reference in its entirety.

Three consecutive aerosolizations were performed for each formulation. At the end of the deposition experiment, the FSI was disassembled and two different procedures were adopted depending on the API under examination.

BDP deposited on each stage of the impactor was recovered with aliquots of water, which were finally transferred into volumetric flasks of adequate volume and made-up to volume with water. The obtained solutions were filtered through a cellulose acetate syringe filter (porosity 0.45 μm and diameter 2.5 cm, GVS Filter Technology, USA) before being analysed. A volumetric flask was used to collect the salbutamol sulphate remained in the RS01® device and in the capsules which were dissolved in water at the end of the experiment in order to ensure complete recovery of the active ingredient. Therefore, in this case, the absorbance initially recorded was corrected by subtracting the contribution due to the absorbance of the Quali-V-I® capsules.

BDP was recovered from each stage of the impactor with appropriate volumes of a methanol/water 6:4 v/v solution. Before being transferred into vials, the solutions were filtered through a regenerated cellulose syringe filter (porosity μm, diameter 2.5 cm, Analytical Technology, Italy).

It was assessed by HPLC.

All the mixtures were tested in triplicate immediately after preparation. Their performance was evaluated by calculating:
  emitted dose (ED), obtained as the sum of the portions of drug recovered from the induction port, the CFC stage and FFC stage expressed in μg, and its percentage with respect to the nominal dose;
  fine particle mass (FPM), namely the quantity of drug with a cut-off diameter lower than 5 μm, calculated by interpolation according to the European Pharmacopoeia (Ph. Eur. 8.0, 2.9.18., which is incorporated herein by reference in its entirety) and expressed in μg;
  the fine particle fraction (FPF), calculated as the ratio of the FPM to the ED expressed as percentage.

The results of the aerosol performances are reported in Table 4.

TABLE 4

| High Dose BDP + carrier (1 + 9 mg) | ED μg | ED % | FPM μg | FPF % |
|---|---|---|---|---|
| 425 μm granules | 666.7 ± 33.7 | 82.9 ± 75.1 | 251.2 ± 1.9 | 41.6 ± 2.8 |
| 425 μm granules + 10% fine <45 μm (pre-granulation) | 609.1 ± 75.1 | 66.0 ± 3.5 | 270.4 ± 47.5 | 44.2 ± 2.4 |
| 425 μm granules + 10% fine <45 μm (post-granulation) | 668.3 ± 19.4 | 76.1 ± 4.4 | 321.8 ± 14.2 | 48.2 ± 3.5 |
| 425 μm granules + 10% | 694.5 ± 3.0 | 71.0 ± 1.6 | 292.5 ± 15.1 | 42.1 ± 2.0 |

TABLE 4-continued

| High Dose BDP + carrier (1 + 9 mg) | ED µg | ED % | FPM µg | FPF % |
|---|---|---|---|---|
| Preblend (post-granulation) 425 µm granules + 30% fine <45 µm (post-granulation) | 666.5 ± 64.4 | 82.1 ± 5.5 | 233.9 ± 45.1 | 35.6 ± 7.9 |

As it can be appreciated, good aerosol performances were obtained with all the preparations, with FPF significantly higher than 35%.

Example 8—Comparative Example—Microwave Preparation of Lactose Granules Using Water as Binder Solution Lactohale LH100 was wetted with a different amount of water in order to obtain a slurry. Slurry samples were prepared by mixing the following amount lactose and water with a mortar:
2 g di LH100+5% w/w H2O;
2 g di LH100+10% w/w H2O;
2 g di LH100+15% w/w H2O;
2 g di LH100+20% w/w H2O.

All the slurries were put in a 50 ml capacity crystallizer and then dried in the microwave (MicroFAST-Microwave-Vacuum Moisture Analyzer, Milestone, USA) at 250 Watt for 5 minutes.

As a first approach, lactose Lactohale LH100 was wetted with an increasing amount of water used as binder. The purpose was to assess the suitable amount of liquid in order to obtain a slurry while not dissolving the lactose in order to avoid the formation of amorphous material during the drying process. After the samples production, a dimensional analysis with sieves was performed to investigate the particle size of the carriers in order to figure out what was the most suitable amount of water to use in the process.

However, lactose powder produced with 5% of water presents the same particle size distribution of the raw material, while the addition of a percentage of water higher than 5% w/w lead to the formation of strong and big aggregates.

Example 9—Comparative Example—Design of Experiment (DoE) Approach to Produce Lactose Granules The design of experiments (DoE) method was used to speed-up the research plan in order to identify significant factors affecting the process and the product quality attributes. The optimization was based on three process factors, namely water percentage, microwave power (W) and drying time (min). Given that three input variables at two levels were considered for the selected material, a fractional factorial 2-level DoE was adopted using the UNSCREMBLER® X 10.3 software (Camo software, Norway) for the study. The 2-level design incorporating 3 parameters plus two central points required 2³+2=10 total experiments for each material to be tested. To investigate how the process affects the material performance, this experimental research was focused on the three outputs:
1) percentage of water lost during the microwave drying process;
2) yield of the process (% of powder with size >180 µm, as determined by sieving and
3) friability determined using a modified friability test for tablets reported in the Ph. Eur. 8.0 2.9.7., which is incorporated herein by reference. Here the friability test was carried out by substituting the standard cylinder of the friabilometer with a plastic jar having a volume of 100 ml rotated at 100 rpm for 4 minutes after loading in the apparatus the total amount of powder resulting from the sieving through the 180 µm sieve. Tables 5 and 6 illustrate the results of a fractional factorial design with central point conducted on Respitose ML006 and Lactohale LH100 respectively.

TABLE 5

| | Input variables | | | Output variables | | |
|---|---|---|---|---|---|---|
| | Power (W) | Water (%) | Time (min) | Yield (%) | Friabiliy (%) | % Water |
| #1 | 250 | 15 | 10 | 25.12 | 23.47 | 0 |
| #2 | 250 | 15 | 10 | 31.31 | 80.33 | 0 |
| #3 | 600 | 15 | 5 | 66.84 | 84.86 | 0 |
| #4 | 600 | 15 | 5 | 45.18 | 80.46 | 0 |
| #5 | 250 | 25 | 5 | 0² | 100 | 9.05 |
| #6 | 250 | 25 | 5 | 0² | 100 | 9.5 |
| #7 | 600 | 25 | 10 | 6.15 | 54.55 | 0 |
| #8 | 600 | 25 | 10 | 8.76 | 38.89 | 0 |
| #9 | 425 | 20 | 7.5 | 41.12 | 74.68 | 0 |
| #10 | 425 | 20 | 7.5 | 32.14 | 22.13 | 0 |

²The powder was too wet to pass through the 180 µm sieve.

TABLE 6

| | Input variables | | | Output variables | | |
|---|---|---|---|---|---|---|
| | Power (W) | Water (% w/w) | Time (min) | Yield (%) <180 µm | Friabiliy (%) | % Water |
| #1 | 250 | 15 | 10 | 26.02 | 49.02 | 0.1 |
| #2 | 250 | 15 | 10 | 31.31 | 80.33 | 0.1 |
| #3 | 600 | 15 | 5 | 15.81 | 6.67 | 0 |
| #4 | 600 | 15 | 5 | 20.51 | 43.69 | 0 |
| #5 | 250 | 25 | 5 | 0³ | 100 | 13.30 |
| #6 | 250 | 25 | 5 | 0³ | 100 | 15.01 |
| #7 | 600 | 25 | 10 | 6.31 | 69.24 | 0 |
| #8 | 600 | 25 | 10 | 64.66 | 63.66 | 0 |
| #9 | 425 | 20 | 7.5 | 32.00 | 32 | 0 |
| #10 | 425 | 20 | 7.5 | 46.57 | 46.57 | 0 |

³The powder was too wet to pass through the 180 µm sieve.

The outcome results for both Respitose ML006 and Lactohale LH100 showed a very high friability except the sample #3 for Lactohale LH100 that showed a value around 7%.

Example 10—Determination of the Loading Capacity

The loading capacity for the granules of the invention can be estimated by mixing it with increasing concentrations of fine lactose particles (Lacto-Sphere MM3 from Micro-Sphere Sa, Switzerland) with a diameter lower than 10 micron, sieving the mixtures and measuring their angle of repose. For comparative purposes, a coarse carrier having a diameter of 212 to 355 microns as reported in WO 01/78693, which is incorporated herein by reference in its entirety, was used.

The mixing operations have been performed with a low shear tumbling mixer (Turbula T2F, WAB, Switzerland) in a 250 ml bin containing 50 g of powder mixture. The mixing process is intentionally designed to be long and gentle offering enough time to the fines particles to meet free carrier surface regions and accommodate on them, the mixing speed has been set to 23 revolutions per minute for a total time of 6 hours. When, increasing the concentration of fine lactose particles, the loading capacity of the carrier saturates, aggregates appear in the blend. Sieving the blends after mixing, with appropriate sieve sizes, the aggregates of fine lactose particles and free fines can be separated from the blended mixture: aggregates remain on the larger sieve, free fines pass the second sieve, while the blend remains on the second sieve.

Due to the difference in particle size the sieves used to separate non-bonded fines, for the carrier of the prior art have a mesh of 180 and 400 μm whereas for the granules of the present invention 180 and 710 μm have been used. As non-bonded fines appear between 20-25% w/w for the carrier of the prior art and between 35-40% w/w for the granules of the invention we can conclude the latter has a larger loading capacity quantifiable as equal to or higher than 15% w/w.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A granule of a physiologically acceptable excipient to be used as a carrier for a dry powder formulation for inhalation, said granule having a mass diameter of from 200 to 800 micrometers and having on its surface pores with a perimeter of from 70 to 300 micrometers and a diameter of from 30 to 100 micrometers, a specific surface area of 0.13 to 0.20 m$^2$/g, and a loading capacity equal to or higher than 35%, wherein said physiologically acceptable excipient is selected from the group consisting of lactose, mannitol, trehalose, dextran, glucose, and mixtures thereof; wherein said granule has a friability of less than 3%.

2. The granule according to claim 1, which is in the form of an agglomerate consisting of a plurality of crystals fused to one another.

3. The granule according to claim 1, wherein said mass diameter is from 300 to 600 micrometers.

4. The granule according to claim 1, wherein said mass diameter is from 400 to 500 micrometers.

5. The granule according to claim 1, wherein said perimeter of said pores is from 100 to 220 micrometers and said diameter of said pores is from 30 to 80 micrometers.

6. The granule according to claim 1, wherein said physiologically acceptable excipient is alpha-lactose monohydrate or mannitol.

7. The granule according to claim 1, obtainable by a process comprising:
(i) selecting particles of a physiologically acceptable excipient having a starting median volume diameter of at least 100 micrometers;
(ii) preparing an oversaturated aqueous solution comprising a part of said physiologically acceptable excipient having a concentration in water of from 30 to 50% w/v;
(iii) wetting the remaining part of said physiologically acceptable excipient with 10 to 25% w/w of said aqueous solution obtained in (ii), to obtain a mixture;
(iv) stirring said mixture to obtain a slurry;
(v) forcing said slurry through a sieve, to obtain a wet mass; and
vi) drying said wet mass to obtain said granules.

8. A pharmaceutical composition in form of dry powder for inhalation, comprising granules according to claim 1 and one or more active ingredients.

9. The pharmaceutical composition according to claim 8, wherein said active ingredient is present in an amount sufficient to deliver a dose, per actuation of the inhaler, equal to or higher than 1 mg.

10. A dry powder inhaler containing a powder pharmaceutical composition according to claim 8.

11. A dry powder inhaler containing a powder pharmaceutical composition according to claim 9.

12. A package, containing a pharmaceutical composition according to claim 8 and a dry powder inhaler.

13. A package, containing a pharmaceutical composition according to claim 9 and a dry powder inhaler.

14. A method of treating a disease or condition of the respiratory tract, comprising administering to a subject in need thereof an effective amount of a pharmaceutical composition according to claim 8.

15. The method accordingly to claim 14, wherein said disease or condition of the respiratory tract is asthma or chronic obstructive pulmonary disease.

* * * * *